(12) United States Patent
Imai

(10) Patent No.: US 8,993,313 B2
(45) Date of Patent: Mar. 31, 2015

(54) ANALYTICAL INSTRUMENT AND ANALYTICAL METHOD

(71) Applicant: ARKRAY, Inc., Kyoto (JP)

(72) Inventor: Toshihiro Imai, Kyoto (JP)

(73) Assignee: ARKRAY, Inc., Kyoto (JP)

( * ) Notice: Subject to any disclaimer, the term of this patent is extended or adjusted under 35 U.S.C. 154(b) by 0 days.

(21) Appl. No.: 13/650,157

(22) Filed: Oct. 12, 2012

(65) Prior Publication Data

US 2013/0109038 A1 May 2, 2013

(30) Foreign Application Priority Data

Oct. 31, 2011 (JP) .................................. 2011-239659
Jul. 9, 2012 (JP) .................................. 2012-153787

(51) Int. Cl.
*C12M 1/34* (2006.01)
*C12Q 1/26* (2006.01)

(52) U.S. Cl.
CPC ...................................... *C12Q 1/26* (2013.01)
USPC ............... 435/288.7; 435/4; 435/10; 435/17; 435/25; 435/28; 435/283.1; 435/287.1

(58) Field of Classification Search
None
See application file for complete search history.

(56) References Cited

U.S. PATENT DOCUMENTS

| 4,287,995 A | * | 9/1981 | Moriya ........................ 215/228 |
| 4,931,387 A |   | 6/1990 | Yamao et al. |
| 5,654,164 A | * | 8/1997 | Gardiol et al. .................. 435/25 |

FOREIGN PATENT DOCUMENTS

| CN | 1910457 A    | 2/2007  |
| JP | H04-076679 B2 | 12/1992 |
| WO | 00/11205 A1  | 3/2000  |

OTHER PUBLICATIONS

Extended European Search Report issued in corresponding European Patent Application No. 12190371.0 dated May 14, 2013.
Office Action issued in corresponding European Patent Application No. 12190371.0 dated Jan. 23, 2014.
Office Action issued in counterpart Chinese Patent Application No. 201210437691.2 dated Jul. 1, 2014.

* cited by examiner

*Primary Examiner* — Satyendra Singh
(74) *Attorney, Agent, or Firm* — Morgan, Lewis & Bockius LLP

(57) ABSTRACT

Provided are an analytical instrument and an analytical method that allow for the direct analysis of a target substance in an undiluted specimen by a transmission photometry in a tightly closed cell container space. An analytical instrument is an analytical instrument for analyzing a target substance contained in a specimen flown in the tightly closed cell container by utilizing an oxidative color-developing agent and an oxidative enzyme reaction, in which an upper substrate and a lower substrate are arranged facing each other and at least a part of the upper substrate and/or at least a part of the lower substrate are/is made of a material transmitting light used for the analysis and having oxygen transmission properties.

7 Claims, 6 Drawing Sheets

ANALYTICAL INSTRUMENT AND ANALYTICAL METHOD

CROSS-REFERENCE TO RELATED APPLICATION

This application claims the benefit of Japanese Patent Application No. 2011-239659 filed on Oct. 31, 2011 and Japanese Patent Application No. 2012-153787 filed on Jul. 9, 2012, the entire disclosures of which are incorporated by reference herein.

FIELD

The present invention relates to a technique for analyzing a target substance in a specimen using oxidative enzyme reaction.

BACKGROUND

Oxygen is dissolved in solution. To take an example of blood, blood contains oxygen bound to hemoglobin, as well as oxygen as dissolved oxygen. For example, detection and analysis of a target substance in blood (particularly in serum or plasma) employs a measurement system using an oxidative enzyme. The measurement system utilizes oxygen in a reaction solution to allow enzyme reaction to proceed. In this case, in a tightly closed space not in contact with air, oxygen that can be utilized for the reaction is only oxygen already present in the specimen and the reaction solution, and there seems to be almost no additional supply of oxygen.

However, in such a state without any oxygen supply, problem can occur when a reagent for analyzing the target substance is a dry reagent, reaction space is the tightly closed space, and then, specimen is flowed in without being diluted. Specifically, it is very unlikely that an intended concentration range of the target substance can be obtained by using only the dissolved oxygen. For example, the amount of dissolved oxygen in blood is approximately from 0.6 to 0.7 mmol/L. However, when considering an example of uric acid or creatinine as a target substance to be measured in a blood specimen, the concentration of uric acid or creatinine, respectively, is approximately 10 mg/gL or 7 mg/dL. That is, since a generally required measurement range for both uric acid and creatinine is 0 to 20 mg/dL, the measurement system as described above cannot satisfy specifications required by the market. Thus, in such a case, instead of using the specimen in its undiluted state, the specimen may be diluted up to an oxygen concentration capable to utilize an oxidative enzyme to supplement oxygen supply before reaction for analysis of a target substance.

Meanwhile, Examined Japanese Patent Application Publication No. H4-76679 has disclosed an analytical instrument in which oxidative enzyme reaction is similarly utilized not in a tightly closed space but in an open system. The analytical instrument uses a dry reagent layer and has an oxygen supply layer between a support and the reagent layer. In addition, the oxygen supply layer has a porous hydrophobic structure because of suppression of uneven color development. The Patent Literature has stated that the porous hydrophobic structure is made of nonwoven fabric, hydrophobic woven fabric or paper, metal and nylon mesh, membrane filter, hydrophobically surface-treated glass filter, ceramic, or the like.

SUMMARY

However, the aforementioned technique for supplementing oxygen supply by diluting a specimen with a sample or the like up to an oxygen concentration capable of utilizing an oxidative enzyme needs a dilution solution (such as water or physiological saline). Additionally, in a case of dilution performed by manual operation, complicated operations increase and precision of dispensing is required, so that quantitative errors may occur. Furthermore, even if dilution is automatically operated, a dilution solution is still necessary. In addition, an expensive apparatus (such as an automatic analyzer) having appropriate function is needed.

On the other hand, in the case of the analytical instrument with the open system disclosed in the above Patent Literature, which utilizes an oxidative enzyme and includes the oxygen supply layer having the porous hydrophobic structure, the analysis of a specimen cannot be done in a tightly closed space and thus precision can be lost.

The present invention has been accomplished in view of the above circumstances. It is an object of the present invention to provide an analytical instrument and an analytical method that allow for the direct analysis of a target substance in an undiluted specimen by transmission photometry in a tightly closed cell container space.

The present inventor has devised an analytical system utilizing solution sending by capillary force inside the cell container in the tightly closed space and a substrate(s) transmitting light used for analysis and having oxygen transmission properties, thereby resulting in the completion of the present invention.

An analytical instrument according to a first aspect of the present invention is an analytical instrument for analyzing a target substance contained in a specimen flowed in a tightly closed cell container by utilizing an oxidative color-developing agent and an oxidative enzyme reaction. The analytical instrument includes an upper substrate and a lower substrate arranged facing each other, at least a part of the upper substrate and/or at least a part of the lower substrate being made of a material that transmits light used for the analysis and has oxygen transmission properties.

Preferably, the analytical instrument further includes a dry reagent layer applied and dried on at least a part of a facing surface(s) of the upper substrate and/or the lower substrate, the dry reagent layer being adapted to be dissolved by the flowed-in specimen and including an oxidative enzyme; a liquid sealing member provided between the upper substrate and the lower substrate to keep the cell container tightly closed; and an air hole for allowing the specimen to flow.

More preferably, the material transmitting light used for the analysis and having oxygen transmission properties is oriented polystyrene, polyethylene, or polypropylene.

More preferably, the oxidative color-developing agent is included in the dry reagent layer.

In addition, preferably, the material having oxygen transmission properties has an oxygen transmission rate of 100 $cc/m^2/hr/atm$ or more.

More preferably, an entire surface(s) of the upper substrate and/or the lower substrate are/is made of the material transmitting light used for the analysis and having oxygen transmission properties.

More preferably, the at least a part of the upper substrate and/or the at least a part of the lower substrate made of the material transmitting light used for the analysis and having oxygen transmission properties have/has a thickness of 0.05 to 0.30 mm.

An analytical method according to a second aspect of the present invention is an analytical method using the analytical instrument according to the first aspect of the invention and includes a step of flowing the specimen in the cell container to keep the cell container tightly closed and a step of dissolving the dry reagent layer that is adapted to be dissolved by the specimen and includes an oxidative enzyme into the specimen in the cell container to photometrically measure color development of pigment of the oxidative color-developing agent according to a reaction with the target substance.

The analytical instrument and the analytical method according to the present invention allow for the direct analysis of a target substance in an undiluted specimen by transmission photometry.

BRIEF DESCRIPTION OF THE DRAWINGS

A more complete understanding of this application can be obtained when the following detailed description is considered in conjunction with the following drawings, in which.

DETAILED DESCRIPTION

In the present invention, the words "include", "contain", and "have" shall encompass also the meanings of the word "comprise".

(Analytical Instrument)

Figure 1:
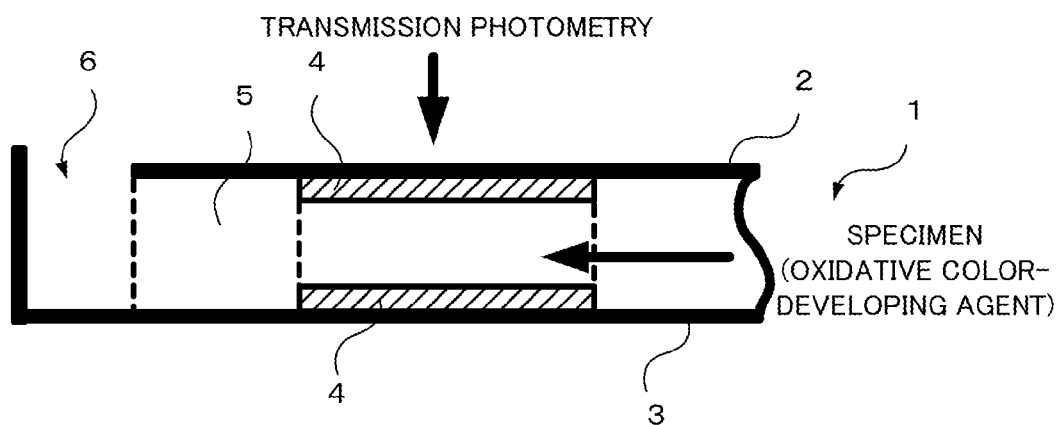
FIG. 1 is a cross-sectional view of an analytical instrument according to Embodiment 1 of the present invention.

Embodiment 1 of the present invention relates to an analytical instrument that utilizes an oxidative color-developing agent, an oxidative enzyme reaction, and a substrate(s) made of a material transmitting light used for analysis and having oxygen transmission properties. Specifically, the analytical instrument of Embodiment 1 is an instrument for analysis (such as detection and measurement of concentration or amount) of a target substance contained in a specimen by supplying oxygen in a cell container. FIG. 1 shows a cross-sectional view of the analytical instrument according to Embodiment 1. As shown in FIG. 1, an analytical instrument 1 includes an upper substrate 2 and a lower substrate 3 arranged facing each other, a dry reagent layer 4 applied and dried on facing sides of the upper substrate 2 and the lower substrate 3 and including an oxidative enzyme, a liquid sealing member 5 provided between the upper substrate 2 and the lower substrate 3 to keep the container tightly closed upon flow of the specimen and an oxidative color-developing agent in the cell container, and an air hole 6 for allowing the specimen and the oxidative color-developing agent to flow.

In the present Embodiment 1, the entireties of the upper substrate 2 and the lower substrate 3 are made of a material transmitting light used for the analysis and having oxygen transmission properties to efficiently supply oxygen in the closed cell, namely in the flowed-in specimen and oxidative color-developing agent. In addition, from the results of Examples described below, the upper substrate 2 and the lower substrate 3 may have a thickness of, for example, approximately 0.05 to 0.30 mm. Examples of the material transmitting light used for the analysis and having oxygen transmission properties, particularly having high oxygen transmission properties, include oriented polystyrene, polyethylene, and polypropylene. In addition, as a modification of Embodiment 1, at least a part of the upper substrate 2 and/or at least a part of the lower substrate 3 may be made of the material transmitting light used for the analysis and having oxygen transmission properties. Additionally, the specimen alone may be flowed in the cell container and the oxidative color-developing agent may be previously applied and dried as the dry reagent layer 4, like an oxidative enzyme. Such a modification structure of the analytical instrument 1 can easily be apparent to those skilled in the art.

The light used for the analysis is not particularly limited as long as the specimen and the oxidative color-developing agent flowed in the cell container dissolve the dry reagent layer 4 and photometry can be performed on the color development of pigment of the oxidative color-developing agent according to a chemical reaction of a target substance by an oxidative enzyme. Specifically, it is only necessary that only a part of a surface of either the upper substrate 2 or the lower substrate 3 be made of the material transmitting light used for the analysis. Alternatively, only a part of both substrates may be made of the material transmitting light used for the analysis. Furthermore, from the results of Examples described below, there may be mentioned a cell optical path length (an optical path length inside the cell container upon photometric measurement) of approximately 100 to 300 μm, for example.

In terms of oxygen transmission properties, as in transmission photometry, it is still most preferable to use the analytical instrument 1 in which the entireties of the upper substrate 2 and the lower substrate 3 are made of a material having high oxygen transmission properties. However, as long as oxidative enzyme reaction can be performed such that a target substance contained in a specimen can be acquired, only a part of the upper substrate 2 and/or only a part of the lower substrate 3 may be made of a material having oxygen transmission properties. Having oxygen transmission properties means that oxygen can be efficiently supplied in the cell container, as in Examples described below. As the degree of oxygen transmission properties (oxygen transmission rate) of the substrate(s), there may be selected one preferable to the flowed specimen and oxidative color-developing agent and to the target substance, such as an oxygen transmission rate of 100 $cc/m^2/hr/atm$ or more. A preferable oxygen transmission rate is 200 $cc/m^2/hr/atm$ or more.

As the dry reagent layer 4, there may also be selected one preferable to the respective specimen and oxidative color-developing agent and the target substance. Alternatively, as mentioned above, the oxidative color-developing agent itself may be included as a part of the dry regent layer 4. Those skilled in the art would be able to easily imagine a component such as an oxidative enzyme in the dry reagent layer 4 in consideration of the oxidative enzyme reaction by those components. In addition, in the present Embodiment 1, the dry reagent layer 4 is applied and dried on both facing surfaces of the upper substrate 2 and the lower substrate 3. However, the dry reagent layer 4 may be applied and dried only on the facing surface of either one of the substrates. Alternatively, the dry reagent layer 4 may be applied only on a part of the upper substrate 2 and/or a part of the lower substrate 3 made of the material transmitting light used for the analysis and having oxygen transmission properties.

The liquid sealing member 5 can be formed using any material in any manner as long as the member can prevent any liquid or the like dissolved in the cell from flowing out. The air hole 6 is necessary to send a fluid specimen or sample by capillary force, which is a known method that allows fluid to be sent not by attraction through a mechanical action such as valve operation but by a natural way of sending fluid.

In the present invention, the term "specimen" means an arbitrary one in a form of solution that can include a target substance to be analyzed. Examples of the specimen include arbitrary and biologically derived or derivable ones such as blood, eye-lens fluid, cerebrospinal fluid, milk, ascitic fluid, bone fluid, peritoneal fluid, amniotic fluid, and cell culture fluid. The specimen can be used directly without being diluted in a state thereof obtained from any one of those examples. In the present invention, the term "target substance" means an arbitrary one that is contained in the specimen to become a target substance of an oxidative enzyme reaction. In other words, the target substance may be any substance as long as the substance undergoes a chemical reaction by an oxidative enzyme contained in the dry reagent layer 4 dissolved and then allows for the detection and analysis of the amount or concentration thereof by photometric measurement on the color development of the oxidative color-developing agent. Examples of the target substance include uric acid (UA) and creatinine (CRE), as mentioned above.

(Analytical Method)

Embodiment 2 of the present invention relates to an analytical method using the analytical instrument 1 according to the invention formed as described above. Specifically, the analytical method includes a step of flowing a specimen in the cell container of the analytical instrument 1 to keep the cell container tightly closed and a step of dissolving, in the cell container 4, the dry reagent layer 4 applied and dried on at least a part of a facing surface(s) of the upper substrate 2 and/or the lower substrate 3 to detect color development of pigment of an oxidative color-developing agent according to the reaction of a target substance by an oxidative enzyme though transmission photometry.

As described above, at least a part of the upper substrate 2 and/or at least a part of the lower substrate 3 of the analytical instrument 1 used in the analytical method of the present Embodiment 2 are/is made of a material having oxygen transmission properties, and preferably a material having high oxygen transmission properties. Accordingly, oxygen is efficiently supplied in the specimen and the dissolved dry reagent layer 4 in the tightly closed cell. The supplied oxygen reacts with the target substance in the specimen by the oxidative enzyme, resulting in that the reaction product causes color development of pigment of the oxidative color-developing agent. Furthermore, as described above, the at least a part of the upper substrate 2 and/or the at least a part of the lower substrate 3 of the analytical instrument 1 are/is made of the material transmitting light used for the analysis. This allows for the transmission photometric analysis (such as detection and measurement of concentration or amount) of the target substance contained in the specimen using color development of the pigment. In addition, since oxygen is efficiently supplied in the tightly closed cell, it is unnecessary to set a limit to a concentration range of the target substance. In brief, the analysis of specimen can be performed without being undiluted.

Next, Examples of the present invention will be described, although the invention is not limited thereto.

Figure 2:
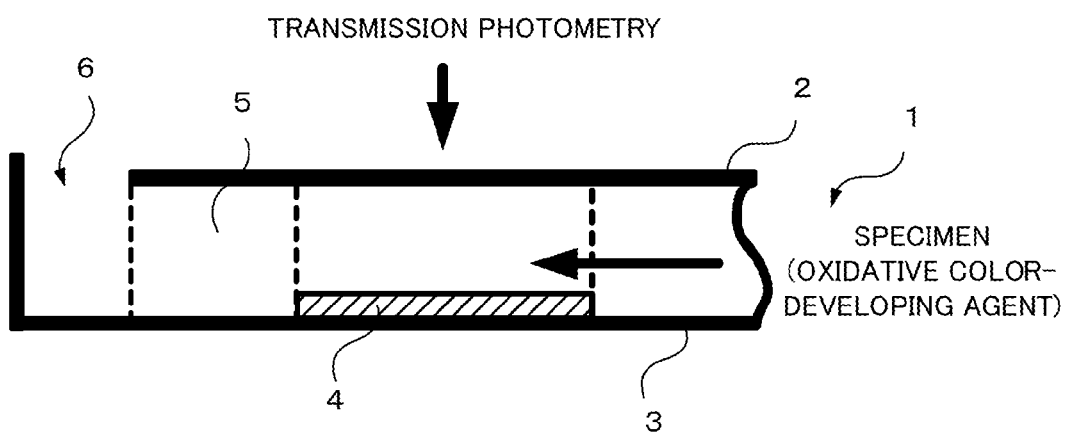
FIG. 2 is a cross-sectional view of an analytical instrument according to Example 1 and Comparative Example 1.

The present Examples and Comparative Examples produced the analytical instrument 1 shown in FIG. 1 or 2 to perform experiments regarding oxygen supply in various situations.

(Example 1 and Comparative Example 1)

FIG. 2 is a cross-sectional view of an analytical instrument according to Example 1 and Comparative Example 1. In Example 1 and Comparative Example 1, the upper substrate 2 of FIG. 2 was formed using each of two kinds of base materials having different oxygen transmission rates to verify the reaction velocity of oxidative enzyme reaction.

First, a brief description will be given of portions common between the Example and the Comparative Examples. In both Examples, the lower substrate 3 is made of polyethylene terephthalate (PET), which is one of polyesters. The cell optical path length (the optical path length inside the cell container upon photometric measurement) was set to 0.288 mm. The cell container had a photometry portion diameter (a diameter inside the cell container upon photometry) of 0.25 mm. The dry reagent layer 4 was applied and dried only on the lower substrate 3. A main reaction component of the dry reagent layer 4 is a mixture of 3-(N-morpholino) propanesulfonic acid: MOPS (pH 7.5) buffer, uricase, and 4-aminoantipyrine. The target substance of the specimen used was uric acid, which was mixed with peroxidase and N-(2-hydroxy-3-sulfopropyl)-3,5-dimethoxyaniline (HDAOS) as an oxidative color-developing agent to be flowed in the cell container. That is, the oxidative enzyme reaction utilized was a uric acid measurement-based reaction scheme. In the reaction scheme, first, uric acid+$O_2$+$H_2O$ turned into allantoin+$H_2O_2$+$CO_2$ by uricase. Then, the oxidative color-developing agent+$H_2O_2$ turned into an oxidative chromogen by peroxidase, where changes over time in the concentration of uric acid were measured based on absorbance according to the color development.

The upper substrate 2 used in Example 1 was made of oriented polystyrene (OPS manufactured by Asahi Kasei Chemicals Corporation) having a thickness of 0.05 mm. The oriented polystyrene has a high oxygen transmission rate of approximately 200 cc/$m^2$/hr/atm. The upper substrate 2 used in Comparative Example 1 was made of the same polyethylene terephthalate (PET) as that of the lower substrate 3 and had a thickness of 0.15 mm. The polyethylene terephthalate had a low oxygen transmission rate of approximately 3 cc/$m^2$/hr/atm.

In the analytical instrument 1 of FIG. 2 produced using each of the upper substrates 2 thus formed was flowed a solution prepared by appropriately mixing the specimen, the oxidative color-developing agent or the like described above. Thereby, inside the cell of the analytical instrument 1, the dry reagent layer 4 was dissolved and thus the uric acid measurement-based reaction scheme as mentioned above occurred. Then, pigment color development according to the reaction was analyzed by transmission photometry.

Figure 3:
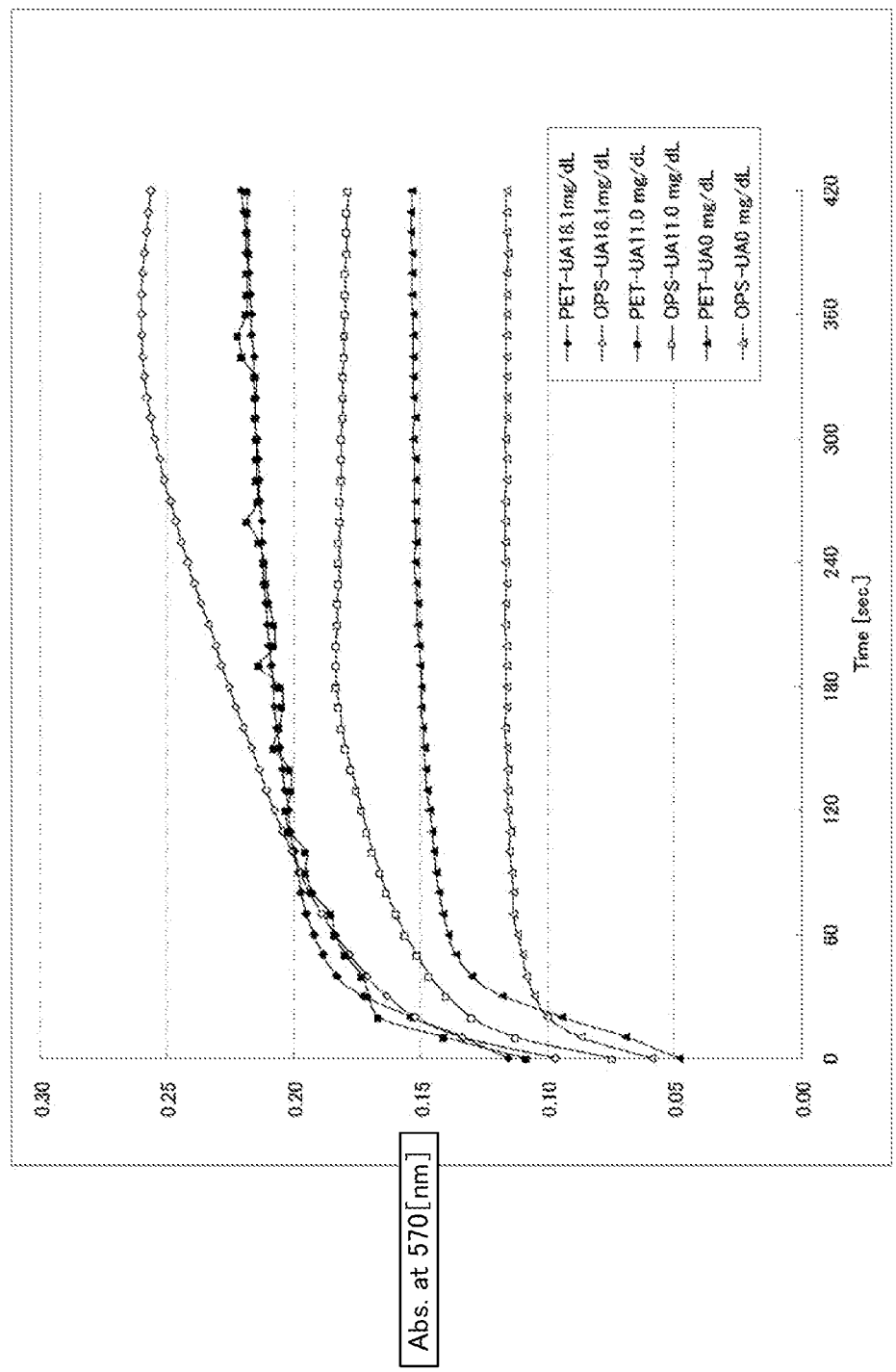
FIG. 3 is a graph showing reaction time courses of absorbance monitored by transmission photometry according to Example 1 (OPS) and Comparative Example 1 (PET)

FIG. 3 is a graph showing reaction time courses of absorbance obtained by transmission photometry according to Example 1 (OPS) and Comparative Example 1 (PET). In FIG. 3, UA 18.1 mg/dL, UA 11.0 mg/dL, or UA 0 mg/dL is the concentration of uric acid (UA) contained in the flowed-in solution. In addition, the horizontal axis represents time and the vertical axis represents absorbance at a wavelength of 570 nm. As shown in FIG. 3, in the case of polyethylene terephthalate (PET) in Comparative Example 1, after consumption of dissolved oxygen in the solution prepared by appropriately mixing the specimen and the like, oxygen was hardly supplied and reaction by uricase leveled off, which is, in other words, not necessarily the results of reaction of the entire uric acid (US) contained in the flowed-in solution. On the other hand, in the oriented polystyrene (OPS) of Example 1, oxygen was supplied in the solution in the cell of the analytical instrument 1 at a constant velocity from outside, thus resulting in an arrival at an endpoint in a reaction state of the entire uric acid (UA) in the flowed-in solution. Accordingly, oxygen supply is dependent on the oxygen transmission rate of substrate material. Therefore, it was confirmed that the use of a substrate made of a material having oxygen transmission properties, particularly having higher oxygen transmission rate allows for the accurate analysis of a target substance contained in a specimen.

(Example 2)

In Example 2, as in Example 1 described above, the upper substrate 2 of FIG. 2 was made of oriented polystyrene (OPS manufactured by Asahi Kasei Chemicals Corporation), whereas the substrate thickness and the cell optical path length were changed to perform the same experiment and compare endpoint arrival times.

The present Example 2 also produced the analytical instrument 1 of FIG. 2. The lower substrate 3, the dry reagent layer 4, the specimen, the oxidative color-developing agent, the reaction scheme were the same as those in Example 1 described above. The thicknesses of the oriented polystyrene (OPS) of upper substrates 2 used were 0.21 mm and 0.05 mm as in Example 1, and the respective cell optical path lengths were 0.463 mm and 0.288 mm.

In the analytical instrument 1 formed by using each of the upper substrates 2 was flowed a solution prepared by appropriately mixing the specimen, the oxidative color-developing agent and/or the like described above. In addition, as a control Example, there was prepared a solution by appropriately mixing a specimen containing no uric acid (UA), the oxidative color-developing agent, and/or the like to perform the same experiment. Thereby, inside the cell of the analytical instrument 1, the dry reagent layer 4 was dissolved and the uric acid measurement-based reaction scheme occurred as mentioned above. After that, color development of pigment according to the reaction was analyzed by transmission photometry.

Figure 4:
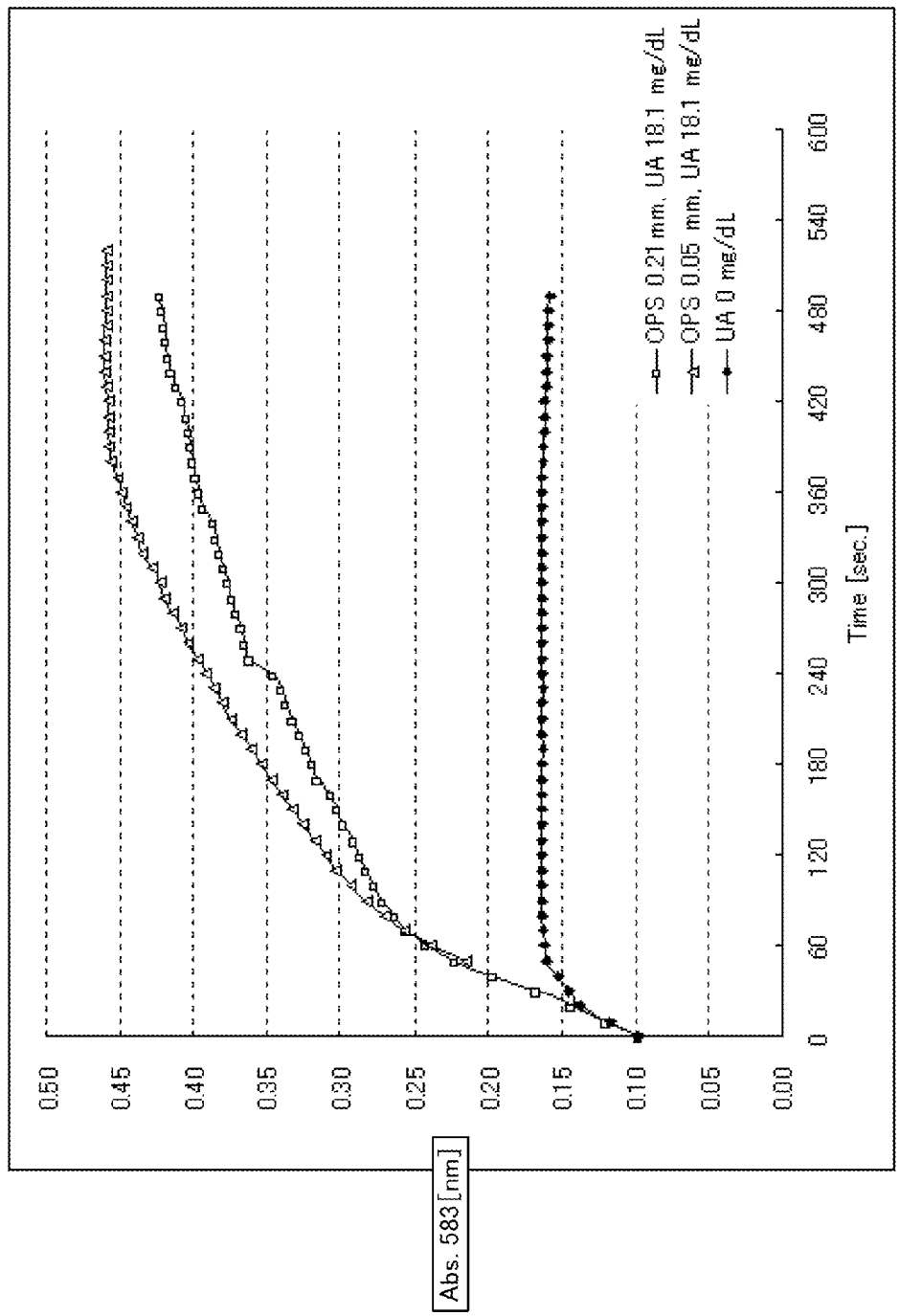
FIG. 4 is a graph showing reaction time courses of absorbance obtained by transmission photometry according to Example 2.

FIG. 4 is a graph showing reaction time courses of absorbance obtained by transmission photometry according to Example 2. The horizontal axis represents time and the vertical axis represents absorbance at a wavelength of 583 nm. As shown in FIG. 4, the upper substrate 2 made of the oriented polystyrene with the thickness of 0.05 mm arrived at an endpoint faster than that made of the oriented polystyrene with the thickness of 0.21 mm. Therefore, the smaller the thickness of the substrate made of a material having oxygen transmission properties, the shorter the endpoint arrival time.

(Example 3)

Example 3 produced the analytical instrument 1 shown in FIG. 1, in which both of the upper substrate 2 and the lower substrate 3 were made of oriented polystyrene (OPS manufactured by Asahi Kasei Chemicals Corporation) having a thickness of 0.13 mm. The dry reagent layer 4 applied and dried on the lower substrate 3 was the same as that in Embodiment 1, whereas on the upper substrate 2 were applied HDAOS as the oxidative color developing agent and peroxidase to form the dry regent layer 4. In brief, only uric acid as the target substance in the specimen was flowed in the cell container.

Although other elements such as the reaction scheme were the same as those in Example 1 described above, the same experiment was performed at different cell optical path lengths (0.200 mm, 0.275 mm, and 0.536 mm) to verify endpoint arrival times.

Figure 5:
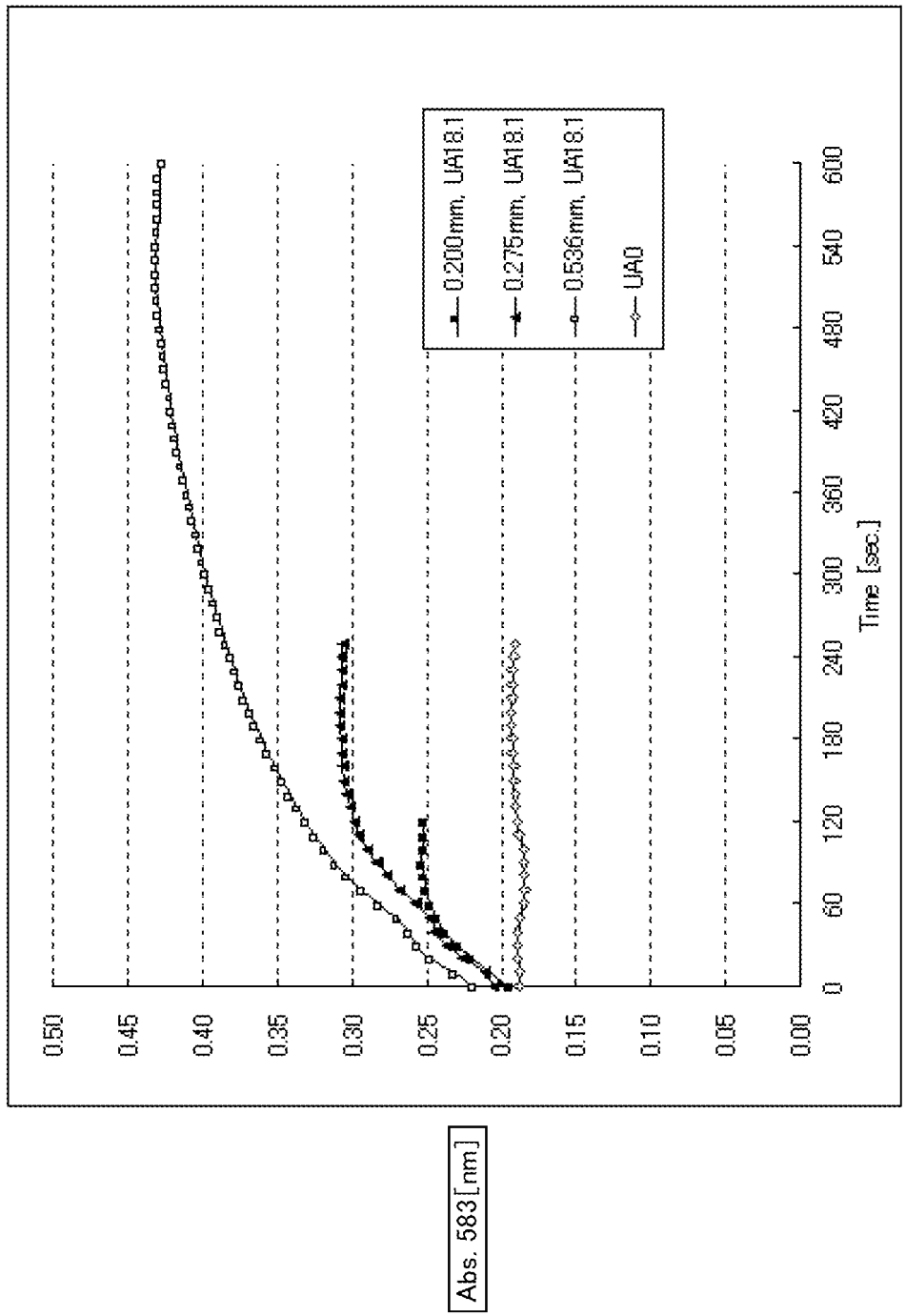
FIG. 5 is a graph showing reaction time courses of absorbance obtained by transmission photometry according to Example 3.

FIG. 5 is a graph showing reaction time courses of absorbance obtained by transmission photometry according to Example 3. The horizontal axis represents time and the vertical axis represents absorbance at a wavelength of 583 nm. As shown in FIG. 5, as the cell optical path length (a depth inside the cell) became shorter, the endpoint arrival time became shorter. This seems to be due to that as the cell optical path length is shorter, the amount of oxygen supplied and the concentration of dissolved oxygen become larger, thus accelerating the oxidative enzyme reaction.

(Example 4)

In Example 4, as in Example 1 described above, the upper substrate 2 of FIG. 2 was made of oriented polystyrene (OPS manufactured by Asahi Kasei Chemicals Corporation), whereas different substrate thickness and different cell optical path lengths were set to perform the same experiment so as to verify a relationship between the substrate thickness, the cell optical path length, and endpoint arrival time.

The present Example 4 also produced the analytical instrument 1 shown in FIG. 2. The lower substrate 3, the dry reagent layer 4, the specimen, the oxidative color-developing agent, and the reaction scheme were the same as those in Example 1 as above. As the upper substrate 2 made of oriented polystyrene (OPS), there were used those having respective thicknesses of 0.05, 0.13, 0.21, and 0.30 mm for verification. In addition, the photometry portion diameters of cells used were all 0.25 mm, whereas the cell optical path lengths thereof were 0.10 mm (capacity inside the cell: 0.49 µL), 0.20 mm (capacity inside the cell: 0.98 µL), 0.275 mm (capacity inside the cell: 1.35 µL), 0.388 mm (capacity inside the cell: 1.90 µL), and 0.538 mm (capacity inside the cell: 2.64 µL), respectively.

In the cell containers of the analytical instruments 1 thus formed was flowed a solution prepared by appropriately mixing the specimen and the oxidative color-developing agent, as in Example 1, to measure absorbance at the wavelength of 583 nm. Herein, to compare oxygen supply effectiveness depending on the differences in the thicknesses of the respective upper substrates 2 and in the respective cell optical path lengths, respective endpoint arrival times were measured using a solution with a uric acid (UA) concentration of 36.2 mg/dL. The table below shows the results of the measured endpoint arrival times (sec). In the table, each of the endpoint arrival times at the cell optical path lengths of 0.388 mm and 0.538 mm refers to a time calculated by doubling an endpoint arrival time obtained upon measurement by the inflow of a solution with UA 18.1 mg/dL.

TABLE 1

| | Endpoint Arrival Time (unit: sec) | | | |
|---|---|---|---|---|
| Cell optical path length [mm] | Cell substrate thickness [mm] | | | |
| | 0.05 | 0.13 | 0.21 | 0.3 |
| 0.1 | 180 | 180 | 220 | 240 |
| 0.2 | 230 | 240 | 390 | 450 |
| 0.275 | 320 | 360 | 560 | 690 |
| 0.388 | 590 | 700 | 1200 | 1540 |
| 0.538 | 930 | 1260 | 1720 | 1980 |

Figure 6:
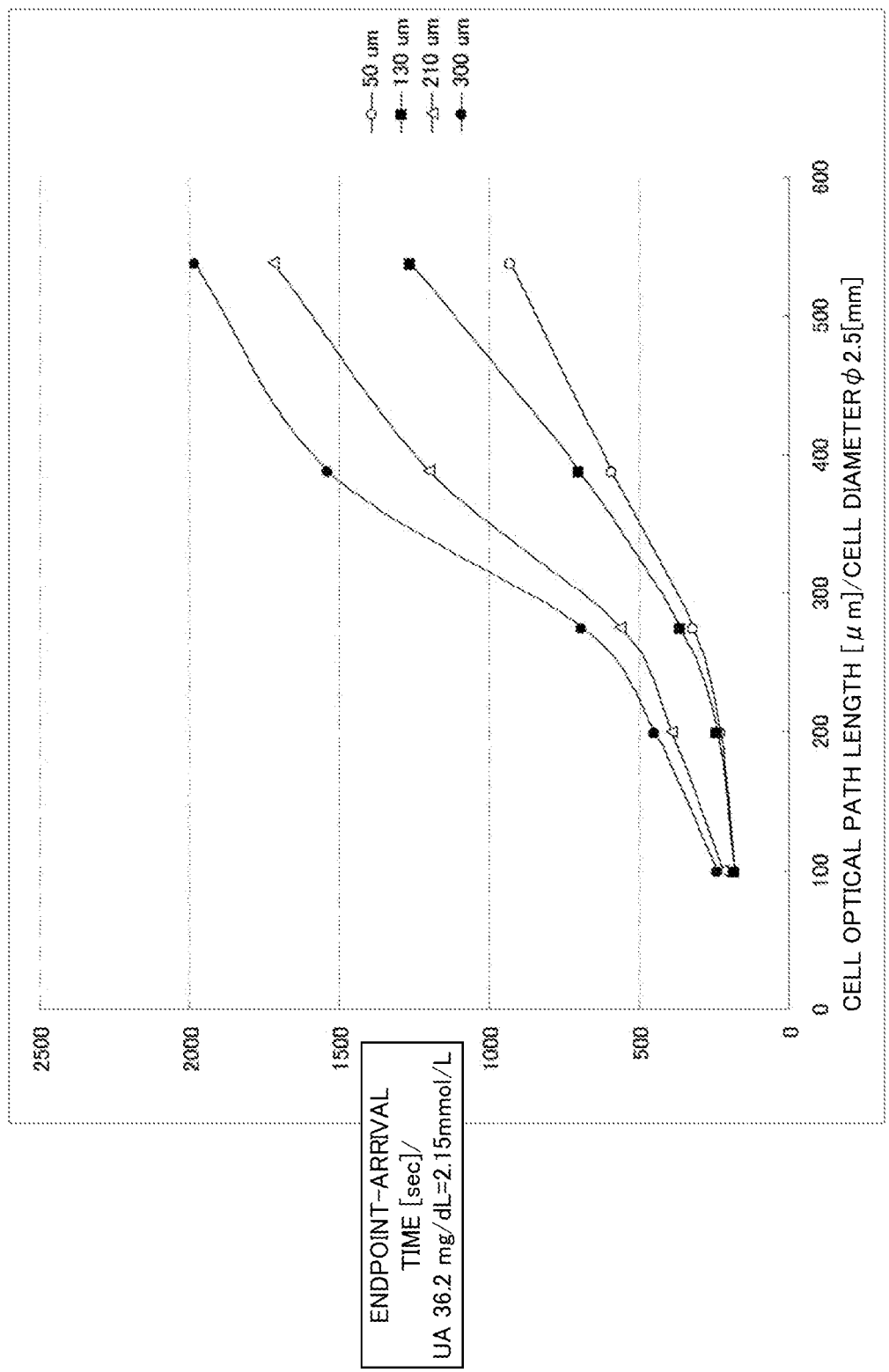
FIG. 6 is a graph showing the results of endpoint arrival time in relation to substrate thickness and cell optical path length according to Example 4.

FIG. 6 shows the results of endpoint arrival times regarding the substrate thicknesses and the cell optical path lengths according to Example 4, which is namely a graph of Table 1. As shown in the graph, it is still expected that as the substrate thickness becomes larger, oxygen supply efficiency becomes worse, leading to prolonged endpoint arrival time. In addition, it is also expected that as the cell optical path length increases, oxygen circulation efficiency in the solution inside the cell is reduced, thus resulting in the prolongation of endpoint arrival time.

It is considered that those results can be utilized, for example, when a specific measurement range of a target substance is known and an analytical instrument 1 allowing measurement within a specific measurement time will be produced. In the example of a target substance such as uric acid (UA) or creatinine (CRE), when an upper limit of the measurement range of the substance is set to 20 mg/dL, to produce an analytical instrument 1 designed with a measurement time up to 5 minutes, it is desirable to select analytical instruments 1 designed with patterns as in Table 2 (uric acid (UA)) and Table 3 (creatinine (CRE)) below. In the Tables, the circle marks represent combinations that can be measured within the measurement range upper limit and the measurement time. In addition, those patterns may be selected depending on the design, and those skilled in the art also would be able to easily select an appropriate pattern for another target substance or the like.

TABLE 2

| Cell optical path length [mm] | Cell substrate thickness [mm] | | | |
|---|---|---|---|---|
| | 0.05 | 0.13 | 0.21 | 0.3 |
| 0.1 | ○ | ○ | ○ | ○ |
| 0.2 | ○ | ○ | ○ | ○ |
| 0.275 | ○ | ○ | ○ | |
| 0.388 | | | | |
| 0.538 | | | | |

TABLE 3

| Cell optical path length [mm] | Cell substrate thickness [mm] | | | |
|---|---|---|---|---|
| | 0.05 | 0.13 | 0.21 | 0.3 |
| 0.1 | ○ | ○ | ○ | ○ |
| 0.2 | ○ | ○ | | |
| 0.275 | ○ | ○ | | |
| 0.388 | | | | |
| 0.538 | | | | |

(Example 5)

In Example 5, there were produced two pieces of the analytical instrument 1 shown in FIG. 1, in which the upper substrates 2 of both analytical instruments 1 were made of oriented polystyrene (OPS) with the thickness of 0.13 mm. However, the oriented polystyrene (OPS) of one of the analytical instruments 1 was manufactured by Asahi Kasei Chemicals Corporation, and the oriented polystyrene (OPS) of the other one thereof was manufactured by Mitsubishi Plastics, Inc., to confirm oxygen supply capabilities depending on the difference between the manufacturers of oriented polystyrene (OPS).

Other structures and components thereof in the two analytical instruments 1 were the same. The lower substrate 3 was made of polyethylene terephthalate (PET) with the thickness of 0.15 mm; the cell optical path length was 0.288 mm; and the photometry portion diameter was 0.25 mm. The main component of the dry reagent layer 4 applied and dried on the upper substrate 2 was a mixture of MOPS (pH 7.5) buffer, uricase, and peroxidase. The main component of the dry reagent layer 4 applied and dried on the lower substrate 3 was an oxidative color-developing agent DA-67.

Figure 7:
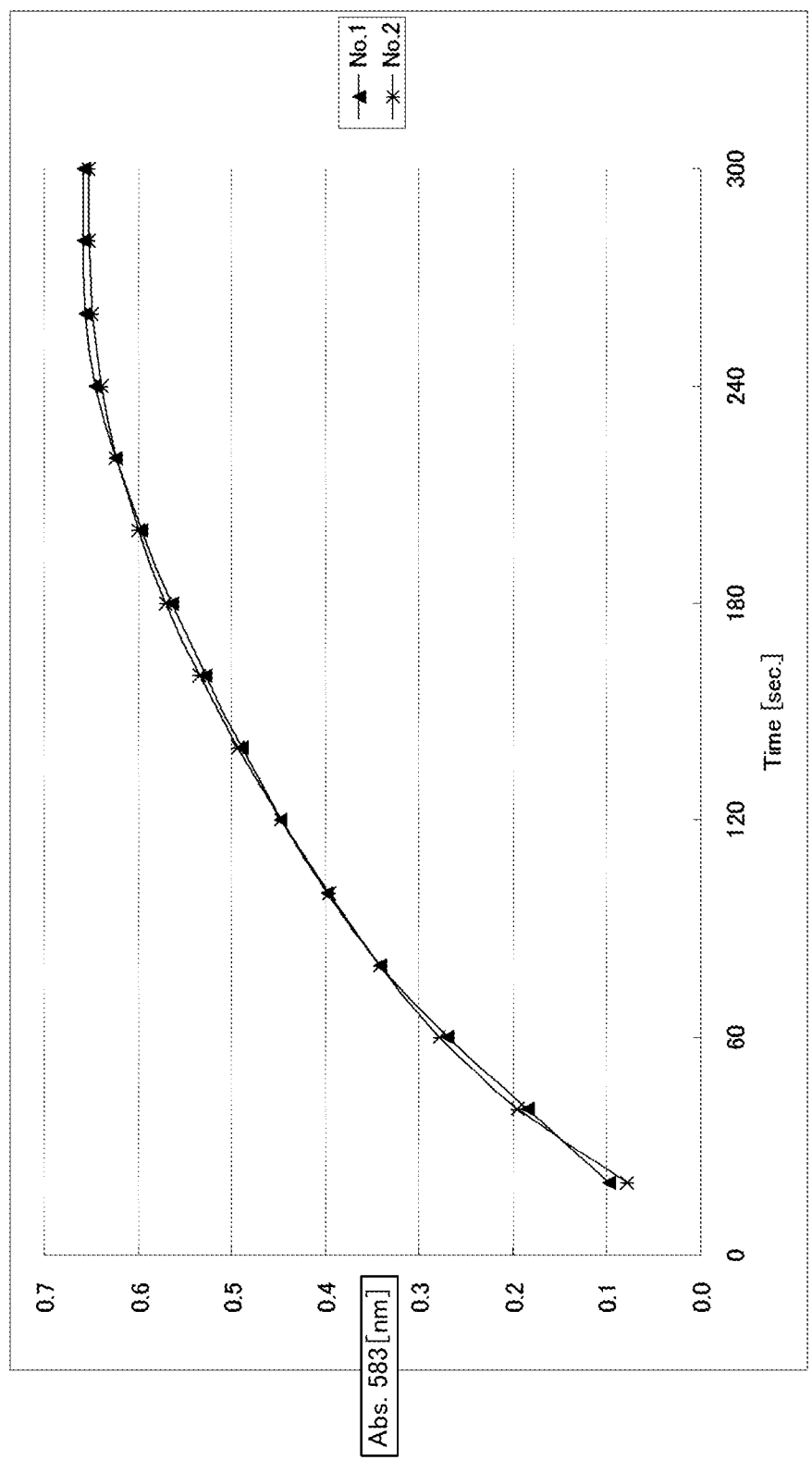
FIG. 7 is a graph showing reaction time courses of absorbance obtained by transmission photometry according to Example 5.

The same reaction scheme as that of Example 1 was used to perform absorbance measurement at a wavelength of 610 nm according to color development in a uric acid concentration of 24.2 mg/dL of a target substance contained in a specimen (serum sample). FIG. 7 is a graph showing reaction time courses of absorbance obtained by transmission photometry according to Example 5. Based on the endpoint arrival times in FIG. 7, comparison was made regarding oxygen supply effectiveness using the respective analytical instruments 1 (No. 1 from Asahi Kasei Chemicals Corporation; No. 2 from Mitsubishi Plastics, Inc.). The results showed that even if the manufacturer of oriented polystyrene (OPS) is different, there is no difference in the oxygen supply capabilities. Accordingly, it was found that the oxygen supply capabilities according to the analytical instruments 1 were basically dependent on the thickness of oriented polystyrene (OPS) and also dependent on oxygen transmission properties associated with the thickness thereof.

The present invention is not limited to the Embodiments of the invention and the Examples thereof at all. Numerous variations and modifications are also included in the invention in a range without departing from the appended claims and easily determined by those skilled in the art.

The entire content of the Examined Japanese Patent Application Publication stated in the present specification is incorporated herein by reference.

Having described and illustrated the principles of this application by reference to one or more preferred embodiments, it should be apparent that the preferred embodiments may be modified in arrangement and detail without departing from the principles disclosed herein and that it is intended that the application be construed as including all such modifications and variations insofar as they come within the spirit and scope of the subject matter disclosed herein.

What is claimed is:

1. An analytical instrument for analyzing a target substance contained in a specimen flowed into a cell container by utilizing an oxidative color-developing agent and an oxidative enzyme reaction, the analytical instrument comprising:
a cell container comprising an upper substrate and a lower substrate arranged to face each other, the upper and lower substrates interleaving a space in which the specimen is flowed, wherein at least a portion of the upper substrate and/or at least a portion of the lower substrate comprises a material that transmits light and oxygen to analyze the target substance;
wherein an open inlet configured to allow the specimen to flow in by capillary force is formed in the cell container, and
an air hole, configured to allow air from inside the cell container to flow out, is formed in the cell container at a site separated from the open inlet by the upper substrate and the lower substrate; and
wherein the analytical instrument further comprises;
a dry reagent layer applied to and dried on at least portions of a facing surface of the upper substrate and/or the lower substrate, the dry reagent layer being dissolved by the flowed specimen and comprising an oxidative enzyme and an oxidative color-developing agent; and
a sealing member provided between the upper substrate and the lower substrate and opposite to the open inlet of the dry reagent layer to prevent a liquid containing the specimen from flowing out of the cell container, wherein the air hole and the dry reagent layer are separated by the sealing member.

2. The analytical instrument according to claim 1, wherein the material is oriented polystyrene, polyethylene, or polypropylene.

3. The analytical instrument according to claim 1, wherein the dry reagent layer comprises the oxidative color-developing agent.

4. The analytical instrument according to claim 1, wherein the material has an oxygen transmission rate of 100 cc/m$^2$/hr/atm or more.

5. The analytical instrument according to claim 1, wherein an entire surface of the upper substrate and/or the lower substrate comprises the material transmitting light and oxygen.

6. The analytical instrument according to claim 1, wherein the at least a portion of the upper substrate and/or the lower substrate comprising said material have/has a thickness of 0.05 to 0.30 mm.

7. A method for analyzing a target substance by the analytical instrument as set forth in claim 1, the method comprising:
 flowing the liquid containing the specimen in the cell container by capillary force to keep the cell container closed;
 contacting and dissolving the dry reagent layer comprising the oxidative enzyme and the oxidative color-developing agent into the specimen in the cell container; and
 photometrically measuring color development of the oxidative color-developing agent resulting from reaction with the target substance.

* * * * *